US010646579B2

(12) United States Patent
Yoneyama

(10) Patent No.: US 10,646,579 B2
(45) Date of Patent: May 12, 2020

(54) COMPLEX COMPRISING RNAI MOLECULE AND N-ACETYLATED CHITOSAN

(71) Applicant: TME THERAPEUTICS INC., Tokyo (JP)

(72) Inventor: Hiroyuki Yoneyama, Tokyo (JP)

(73) Assignee: TME THERAPEUTICS INC., Tokyo (JP)

( * ) Notice: Subject to any disclaimer, the term of this patent is extended or adjusted under 35 U.S.C. 154(b) by 0 days.

(21) Appl. No.: 15/773,352

(22) PCT Filed: Nov. 2, 2016

(86) PCT No.: PCT/JP2016/082545
§ 371 (c)(1),
(2) Date: May 3, 2018

(87) PCT Pub. No.: WO2017/078054
PCT Pub. Date: May 11, 2017

(65) Prior Publication Data
US 2018/0318430 A1 Nov. 8, 2018

(30) Foreign Application Priority Data

Nov. 4, 2015 (JP) .................................. 2015-216482

(51) Int. Cl.
C12N 15/113 (2010.01)
A61K 47/61 (2017.01)
A61K 31/713 (2006.01)
A61K 47/36 (2006.01)
A61K 48/00 (2006.01)
C12N 9/10 (2006.01)
A61P 1/00 (2006.01)
A61P 1/04 (2006.01)

(52) U.S. Cl.
CPC ............ A61K 47/61 (2017.08); A61K 31/713 (2013.01); A61K 47/36 (2013.01); A61K 48/00 (2013.01); A61P 1/00 (2018.01); A61P 1/04 (2018.01); C12N 9/13 (2013.01); C12N 15/1137 (2013.01); C12Y 208/02033 (2013.01)

(58) Field of Classification Search
None
See application file for complete search history.

(56) References Cited

U.S. PATENT DOCUMENTS

2006/0293216 A1 12/2006 Klaveness et al.
2010/0329993 A1 12/2010 Yoneyama et al.
2011/0027248 A1 2/2011 Yoneyama et al.
2015/0087689 A1 3/2015 Merzouki et al.
2015/0337313 A1 11/2015 Yoneyama et al.

FOREIGN PATENT DOCUMENTS

| JP | 10-509207 A | 9/1998 |
|---|---|---|
| JP | 2006-516988 A | 7/2006 |
| JP | 2010-503640 A | 2/2010 |
| JP | 2014-518875 A | 8/2014 |
| WO | WO 96/20730 A1 | 7/1996 |
| WO | WO 2008/031899 A2 | 3/2008 |
| WO | WO 2009/004995 A1 | 1/2009 |
| WO | WO 2009/084232 A1 | 7/2009 |
| WO | WO 2012/159215 A1 | 11/2012 |
| WO | WO 2014/013535 A1 | 1/2014 |

OTHER PUBLICATIONS

International Search Report dated Dec. 6, 2016 in PCT/JP2016/082545, 2 pages.
Hisanori Kiryu, et al., "A Detailed Investigation of Accessibilities Around Target Sites of siRNAs and miRNAs" Bioinformatics vol. 27, No. 13, 2011, pp. 1788-1797.
Kenji Suzuki, et al., "Endoscopic Submucosal Injection of a Synthesized Anti-CHST15 dsRNA for Sulfated Glycosaminoglycan is a Safe and Beneficial Treatment for Patients with Crohn's Disease who do not Respond Sufficiently to the Conventional Treatment" U.S. Digestive Disease Week (DDW), 2014, Abstract, Su1078, p. S-366.
Kenichi Watanabe, et al., "Small Interfering RNA Therapy Against Carbohydrate Sulfotransferase 15 Inhibits Cardiac Remodeling in Rats with Dilated Cardiomyopathy" Cellular Signalling, vol. 27, 2015, pp. 1517-1524.
Makoto Nishimura, et al. "A translational Study to Investigate the Role of Carbohydrate Sulfotransferase 15 for Pancreatic Cancer Biology from in Vitro to First-In-Human Clinical Research" 2015 Annual of the American Society of Clinical Oncology (ASCO Annual Meeting), 2015, Abstract, e22201, 2 Pages.
Makoto Nishimura, et al. "EUS-Guided Intratumoral Injection of CHST15 dsRNA for Unresectable Pancreatic Cancer: An Investigator-Initiated Trial" U.S. Digestive Disease Week (DDW), 2015, Abstract, Mo 1043, 2 Pages.
Makoto Nishimura, "EUS-Guided Intratumoral Injection of CHST15 dsRNA for Unresectable Pancreatic Cancer" United European Gastroenterology Week (UEGW), 2015, Abstract, 5 Pages.
Eriko Kai, et al., "A Method for Oral DNA Delivery with N-Acetylated Chitosan" Pharmaceutical Research, vol. 21, No. 5, May 2004, pp. 838-843.
Shirui Mao, et al., "Chitosan-Based Formulations for Delivery of DNA and siRNA, Advanced Drug Delivery Reviews" vol. 62, 2010, pp. 12-27.
Jostein Malmo, et al., "siRNA Delivery with Chitosan Nanoparticles: Molecular Properties Favoring Efficient Gene Silencing" Journal of Controlled Release, vol. 158, 2012, pp. 261-268.

(Continued)

Primary Examiner — J. E Angell
(74) Attorney, Agent, or Firm — Oblon, McClelland, Maier & Neustadt, L.L.P.

(57) ABSTRACT

Provided is a composition comprising an RNAi molecule which suppresses expression of CHST15 gene and successfully used for less invasive administration. A complex comprising an RNAi molecule which suppresses expression of CHST15 gene and an N-ace.

7 Claims, 7 Drawing Sheets
Specification includes a Sequence Listing.

(56) References Cited

OTHER PUBLICATIONS

Somasundaram Arumugam, et al., "Orally Active siRNA Targeting Carbohydrate Sulfotransferase 15 Alleviates Colonic Mucosal Injury in Mice" Gastroenterology, vol. 150, No. 4, Suppl. 1, Apr. 2016, p. S-125 and cover page.

COMPLEX COMPRISING RNAI MOLECULE AND N-ACETYLATED CHITOSAN

TECHNICAL FIELD

The present invention relates to a complex comprising an RNAi molecule which suppresses expression of CHST15 gene, and an N-acetylated chitosan; a method for producing the complex; and a pharmaceutical composition comprising the complex.

BACKGROUND ART

Diseases causing chronic inflammation or ulceration in the mucosal membrane of the large intestine and small intestine are collectively called inflammatory bowel disease. As the inflammatory bowel disease, ulcerative colitis and Crohn's disease are typically known, which are both intractable diseases. Ulcerative colitis is an inflammatory disease producing ulcer and erosion in the large-intestinal mucosa and exhibiting various systemic symptoms including hemorrhagic diarrhea, abdominal pain and fever. Crohn's disease is an inflammatory disease producing non-continuous ulcer and inflammation throughout the entire alimentary canal tract from the oral cavity to the anus and exhibiting systemic symptoms such as abdominal pain, fever, chronic diarrhea and malnutrition.

A sulfotransferase, more specifically, carbohydrate sulfotransferase 15 (CHST15) (also referred to as GalNAc4S-6ST or N-acetylgalactosamine 4-sulfate 6-O-sulfotransferase), is a type II transmembrane Golgi protein, which transfers a sulfate to the 6-position of a GalNAc ($4SO_4$) residue of chondroitin sulfate-A (CS-A) to synthesize highly sulfated chondroitin sulfate-E (CS-E). The present inventors have reported that submucosal administration of siRNA (CHST15 siRNA) which suppresses expression of CHST15 gene to the large-intestine of an animal model of a colitis, decreases expression of the CHST15 gene in the large intestine and produces therapeutic effects including suppression of ulceration, inflammation and fibrosis; and that the therapeutic effects were also exerted in human patients with Crohn's disease (Patent Literatures 1 to 3 and Non Patent Literatures 1 and 2). In addition, it has been recently reported that CHST15 siRNA locally administered has an effect on dilated cardiomyopathy and pancreatic cancer (Non Patent Literatures 3 to 6).

Since oligonucleotide therapeutics such as siRNA is easily degraded by an enzyme such as nuclease, siRNA is often topically administered to affected sites, for example, by injection or a special drug delivery system. However, the local administration is limited in the administration site and must be carried out by a doctor. Because of this, development of a preparation having a dosage form, that can be simply and less invasively administered to many sites, such as an oral preparation, has been desired.

Chitosan is a high molecular-weight polysaccharide, which can be produced by deacetylation of chitin, a main component of the shell of arthropods such as crustaceans and insects and the cell wall of fungi. Patent Literatures 4 and 5 disclose a composition for delivering siRNA, which contains chitosan and siRNA. However, Patent Literatures 4 and 5 do not disclose that chitosan is acetylated, and the obtained acetylated chitosan is used in combination with siRNA, at all. Non Patent Literature 7 reports that a complex containing an N-acetylated chitosan and plasmid DNA can be delivered to the intestine by oral administration. However, Non Patent Literature 7 does not describe a complex formed of an RNAi molecule such as siRNA in combination with an N-acetylated chitosan, at all.

CITATION LIST

Patent Literature

Patent Literature 1: International Publication No. WO 2009/004995
Patent Literature 2: International Publication No. WO 2009/084232
Patent Literature 3: International Publication No. WO 2014/013535
Patent Literature 4: JP Patent Publication (Kohyo) No. 2010-503640 A (International Publication No. WO 2008/031899)
Patent Literature 5: JP Patent Publication (Kohyo) No. 2014-518875 A (International Publication No. WO 2012/159215)

Non Patent Literature

Non Patent Literature 1: Kiryu H, et al., Bioinformatics 27 (13): 1788-1797 (2011)
Non Patent Literature 2: Suzuki K, et al., U.S. Digestive Disease Week (DDW) 2014, Abstract, Su1078 (2014)
Non Patent Literature 3: Watanabe K, et al., Cell Signal 27 (7): 1517-1524 (2015)
Non Patent Literature 4: Nishimura M, et al., 2015 Annual meeting of the American Society of Clinical Oncology (ASCO Annual Meeting), Abstract, e22201 (2015)
Non Patent Literature 5: Nishimura M, et al., U.S. Digestive Disease Week (DDW) 2015, Abstract, Mo1043 (2015)
Non Patent Literature 6: Nishimura M, United European Gastroenterology Week (UEGW) 2015, Abstract (2015)
Non Patent Literature 7: Kai E, et al., Pharmaceutical Research 21: 838-843 (2004)

SUMMARY OF INVENTION

Technical Problem

An object of the present invention is to provide a composition comprising an RNAi molecule which suppresses expression of CHST15 gene and successfully used in less-invasive administration.

Solution to Problem

The present inventors conducted intensive studies with a view to attaining the aforementioned object. As a result, they surprisingly found that by orally administering a complex comprising N-acetylated chitosan and siRNA which suppresses expression of CHST15 gene, the complex is efficiently delivered to the small intestine and large intestine to suppress expression of CHST15 gene. Furthermore, they found that the complex exerts a therapeutic effect on small intestine inflammation and colitis. Based on the findings, the present invention was accomplished.

The present invention comprises the followings.
[1] A complex comprising an RNAi molecule which suppresses expression of CHST15 gene and an N-acetylated chitosan.
[2] The complex according to [1], wherein the degree of acetylation in the N-acetylated chitosan is 70 to 100%.
[3] The complex according to [1] or [2], wherein the RNAi molecule is siRNA.

[4] The complex according to any one of [1] to [3], wherein the RNAi molecule comprises an antisense strand comprising a nucleotide sequence shown in SEQ ID NO: 1 and a sense strand comprising a nucleotide sequence complementary to the antisense strand.

[5] A method for producing a complex comprising an RNAi molecule which suppresses expression of CHST15 gene and an N-acetylated chitosan, comprising:
(a) mixing the RNAi molecule with chitosan to form a complex;
(b) drying the complex obtained in step (a); and
(c) acetylating the chitosan in the dried complex obtained in step (b).

[6] A pharmaceutical composition comprising the complex according to any one of [1] to [4], for treating or preventing an inflammatory disease or mucosal damage of the digestive tract.

[7] The pharmaceutical composition according to [6], for use in oral administration or transrectal administration.

[8] The pharmaceutical composition according to [6] or [7], wherein the inflammatory disease or mucosal damage is selected from the group consisting of inflammatory bowel disease, ulcerative colitis, Crohn's disease, esophagitis, gastroenteritis, NSAID-induced enteritis, intestinal Behcet's disease, simple ulcer, artificial ulcer after endoscopic resection of alimentary canal cancer, enteritis associated with a connective tissue disease, enteritis by radiation, ischemic enteritis, reflux esophagitis, Barrett's esophagus, drug-induced esophagitis or gastroenteritis, and drug resistant or refractory peptic ulcer.

The present specification incorporates the contents disclosed in JP Patent Application No. 2015-216482, based on which the priority of the present application is claimed.

Advantageous Effects of Invention

According to the present invention, it is possible to provide a composition comprising an RNAi molecule which suppresses expression of CHST15 gene and successively used for less invasive administration.

DESCRIPTION OF EMBODIMENTS

Figure 1:
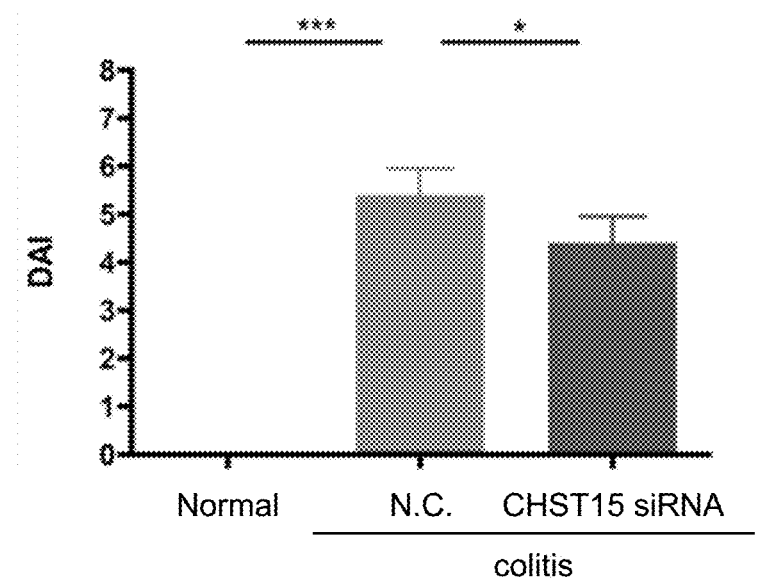
FIG. 1 is a graph showing the disease activity index (DAI) in DSS (dextran sulfate sodium)-induced colitis model mice.

Now, the present invention will be more specifically described below.
<Complex>
The present invention provides a complex comprising an RNAi molecule which suppresses expression of CHST15 gene and an N-acetylated chitosan.

The RNAi molecule to be used in the present invention can suppress expression of CHST15 gene. In the present specification, the CHST15 gene is not particularly limited; however, the CHST15 gene may be derived from an animal, for example, a mammal (e.g., human, monkey, bovine, mouse, rat, dog).

The nucleotide sequence of human CHST15 gene can be obtained, for example under GenBank accession number NM_015892. The nucleotide sequence of human CHST15 gene is shown in SEQ ID NO: 5; the amino acid sequence of CHST15 protein encoded by the gene is shown in SEQ ID NO: 6.

In the present specification, CHST15 protein includes a protein, which has a high identity (for example, 80% or more, preferably 90% or more, more preferably 95% or more or 98% or more) with the amino acid sequence shown in SEQ ID NO: 6, and which has an activity (for example, sulfate transfer activity) of the protein consisting of the amino acid sequence shown in SEQ ID NO: 6. Examples of CHST15 gene include genes encoding a CHST15 protein as mentioned above and present in non-human organisms.

Examples of CHST15 gene also include endogenous CHST15 genes (orthologs of human CHST15 gene), which are present in non-human organisms and correspond to DNA consisting of the nucleotide sequence shown in SEQ ID NO: 5. Those skilled in the art can appropriately obtain endogenous CHST15 genes present in non-human organisms, based on the nucleotide sequence shown in SEQ ID NO: 5. The endogenous CHST15 genes present in non-human organisms can generally possess a high identity (for example, 80% or more, preferably 90% or more, more preferably 95% or more or 98% or more) with DNA shown in SEQ ID NO: 5. For example, the nucleotide sequences of CHST15 genes in a mouse, rat, bovine, and dog can be obtained under GenBank accession number NM_029935.5, NM_173310.3, XM_005225861.2 and XM_544058.6, respectively.

Sequence identity can be appropriately determined by those skilled in the art. Determination of sequence identity may involve aligning two sequences. Examples of the computer program for performing such sequence alignment include, but are not particularly limited to, Vector NTI (registered trade mark) (Thermo Fisher Scientific Inc.) and ClustalW program (Thompson J D, et al., Nucleic Acids Research 22 (22): 4673-4680; Larkin, et al., Bioinformatics 23 (21): 2947-2948 (2007)). ClustalW program is available on the web page of, for example, DNA Data Bank of Japan (DDBJ). After the two sequences are aligned, the sequence identity (%) between them can be calculated. Typically, as a part of a sequence comparison process carried out by the software, the sequence identity is output as a numerical value.

In the present invention, the RNAi molecule can suppress expression of CHST15 gene. In the present specification, "RNAi molecule" refers to an RNA molecule, which can induce RNAi (RNA interference) in vivo, and suppress (silence) the expression of a target gene (CHST15 in the present invention) via, for example, degradation of the transcription product of the gene (Fire A. et al., Nature 391, 806-811 (1998)). Specific examples of the RNAi molecule include siRNA and shRNA. "siRNA" is a double stranded RNA formed by hybridization of an antisense strand comprising a sequence complementary to a part of the mRNA sequence of the target gene with a sense strand comprising a sequence complementary to the antisense strand (homologous to a part of the target gene). "shRNA" is single stranded RNA formed by linking the sense strand with the antisense strand of said siRNA via a short spacer sequence having an appropriate sequence. In other words, shRNA has a stem structure formed by a sense region and an antisense region, which form base-pairing with each other within a single molecule, and at the same time, a loop structure formed by said spacer sequence, thereby forming a hair-pin like step-loop structure as a whole molecule.

In the present specification, suppression of target-gene expression is determined based on the expression level of the target gene, using the expression level of mRNA or protein of the gene as a readout. In this case, suppression of target-gene expression refers to not only 100% suppression but also suppression of 75% or more, 50% or more or 20% or more relative to the case where no RNAi molecule is introduced or irrelevant control RNAi molecule is introduced. The expression level of mRNA can be determined, for example, by northern hybridization or real time PCR; whereas the expression level of a protein can be determined, for example, by western blotting, ELISA or measurement of protein activity. These can be appropriately carried out by those skilled in the art. The method for determining gene expression level is also described in Green, M R and Sambrook, J, (2012) Molecular Cloning: A Laboratory Manual Fourth Ed., Cold Spring Harbor Laboratory Press, Cold Spring Harbor, N.Y.

The sequence of an RNAi molecule can be appropriately designed by those skilled in the art based on the nucleotide sequence of a target gene (CHST15 gene). For example, an antisense strand can be designed such that the antisense strand comprises a sequence complementary to a part of e.g., a coding region or 5' or 3' untranslated region (UTR) of the target-gene mRNA, and a sense strand can be designed such that the sense strand comprises a sequence complementary to the above antisense strand.

In the present specification, being "complementary" refers to a relationship between two bases that can form base-pairing(for example, Watson-Crick type); for example, refers to the relationship between adenine and thymine or uracil, and the relationship between cytosine and guanine. In the present specification, being complementary is preferably being completely complementary, thought this is not always necessary, an RNAi molecule may contain mismatches of one or more bases (for example, 1 to 5 or 1 to 3 bases) as long as it retains the ability to suppress expression of its target-gene expression. "Mismatch" used herein refers to relationships except the relationship between adenine and thymine or uracil and the relationship between cytosine and guanine.

It is generally known that an RNAi molecule such as an siRNA has high RNAi activity if it has a single strand portion (overhang) of several (for example, 2 to 5) nucleotides at an end. Because of this, the RNAi molecule to be used in the present invention preferably has an overhang of several deoxyribonucleotides or ribonucleotides at an end. For example, an RNAi molecule may have a 3' overhang of two nucleotides. Specifically, an RNAi molecule may have a 3' overhang consisting of two ribonucleotides (for example, AU or AG).

A sense strand and an antisense strand constituting an RNAi molecule each may have, for example, but is not particularly limited to, a 20 to 50 base length, a 20 to 40 base length or a 20 to 30 base length. They may have the same lengths or different lengths. In the present invention, the sense strand and antisense strand preferably may each have a 25 to 29 base length, for example, a 27 base length.

Specifically, the RNAi molecule can comprise an antisense strand comprising the nucleotide sequence shown in SEQ ID NO: 1 and a sense strand comprising the nucleic acid sequence complementary to the antisense strand. In this case, the sense strand preferably comprises the nucleotide sequence shown in SEQ ID NO: 2, which is a sequence completely complementary to the sequence shown in SEQ ID NO: 1.

More specifically, the antisense strand may consist of the nucleotide sequence shown in SEQ ID NO: 3, which is a sequence obtained by adding ribonucleotides (AU) to the 3' end of the nucleotide sequence shown in SEQ ID NO: 1. The sense strand may consist of the nucleotide sequence shown in SEQ ID NO: 4, which is a sequence obtained by adding ribonucleotides (AG) to the 3' end of the nucleotide sequence shown in SEQ ID NO: 2.

The nucleotides of the RNAi molecule all are preferably ribonucleotides; however, several (for example, 1 to 5, 1 to 3 or 1 to 2) nucleotides may be deoxyribonucleotides. The nucleotides of the RNAi molecule may be modified nucleotides having a group such as a halogen atom (fluorine, chlorine, bromine or iodine), methyl, carboxymethyl or thio group in addition to natural nucleotides, in order to improve, for example, the stability of the RNAi molecule.

The sense strand and antisense strand constituting the RNAi molecule can be appropriately produced by a commercially available nucleic acid synthesizer. The sense strand and antisense strands thus produced may be preferably mixed an equimolar ratio, and hybridized with each other to produce an RNAi molecule. Also, the RNAi molecule may be produced using contracted manufacturing services of a manufacturer (for example, BioSpring, Takara Bio Inc., Sigma-Aldrich).

Next, the "chitosan" used in the present invention is a high molecular-weight polysaccharide having a structure where glucosamine and a small amount of N-acetyl glucosamine are polymerized. Chitosan can be obtained by deacetylating chitin, which can be obtained from the shell of crustaceans such as crab and shrimp, via heating with a concentrated alkali solution. Chitosans with different degrees of acetylation and molecular weight are commercially available from, for example, Carbosynth Limited or Funakoshi Co., Ltd. In the present specification, the degree of acetylation of chitosan may be usually 0 to 30%, for example, 20% or less, 10% or less or 5% or less. In the present specification, the molecular weight of chitosan is not particularly limited. A low molecular weight chitosan (for example, molecular weight: 2000 Da to 100 kDa), a high molecular weight chitosan (for example, molecular weight: 100 kDa to 10,000 kDa or more) or a mixture of chitosans with different molecular weight may be used.

"N-acetylated chitosan" is a high molecular-weight polysaccharide obtained by acetylating part or whole of the amino groups of chitosan as mentioned above. In the present specification, the degree of acetylation of N-acetylated chitosan may be usually 70 to 100%, for example, 80% or more, 90% or more, 95% or more, 98% or more or 99% or more. The degree of acetylation of chitosan and N-acetylated chitosan can be determined by, e.g., colloid titration, infrared absorption spectrum, nuclear magnetic resonance spectrum (NMR) or element analysis.

In a complex comprising an RNAi molecule which suppresses expression of CHST15 gene and an N-acetylated chitosan, the binding mode of the RNAi molecule and the N-acetylated chitosan is not particularly limited. Since the RNAi molecule is an anionic polymer and the N-acetylated chitosan is a cationic polymer, the two are assumed to form a complex by electrostatic interaction. In the aforementioned complex, the ratio (molar ratio) of the RNAi molecules and glucosamine units constituting the N-acetylated chitosan may be 1:200 to 1:5, 1:100 to 1:5, or 1:50 to 1:10.

An exemplary method for producing a complex comprising an RNAi molecule which suppresses expression of CHST15 gene and an N-acetylated chitosan is described in the following section "Production method". An RNAi molecule can be delivered by the complex of the present invention without requiring a special drug delivery system but by a less invasive administration method, for example, oral administration.

<Production Method>

The present invention also provides a method for producing a complex comprising an RNAi molecule which suppresses expression of CHST15 gene and an N-acetylated chitosan. The present method comprises the steps of: (a) mixing the RNAi molecule with chitosan to form a complex; (b) drying the complex obtained in step (a); and (c) acetylating the chitosan in the dried complex obtained in step (b).

As the chitosan, chitosan having a degree of acetylation of 0 to 30%, for example 20% or less, 10% or less or 5% or less, may be used. Chitosan may be provided as a chitosan solution prepared by dissolving chitosan, for example, in an aqueous acid solution. The type of acid is not particularly limited, but includes e.g., acetic acid or hydrochloric acid, and preferably acetic acid. The aqueous acid solution may have a concentration of, for example, 1% (v/v) to 10% (v/v) and preferably 2% (v/v) to 8% (v/v). Chitosan can be dissolved in an aqueous acid solution in a concentration of 0.1% (w/v) to 10% (w/v) and preferably 1% (w/v) to 8% (w/v). A method for dissolving chitosan in an aqueous acid solution is not particularly limited. Chitosan may be dissolved by a routine method such as stirring. The temperature at the time of dissolution may be room temperature, for example, 15 to 30° C. The dissolution time, which varies depending on, e.g., the molecular weight and degree of acetylation of chitosan, may be appropriately determined. The pH of the chitosan solution thus obtained can be controlled with an alkali solution, for example, a sodium hydroxide solution, to be 3.0 to 5.0, preferably 3.5 to 4.5 and more preferably 4.0 to 4.3. Then, the chitosan solution may be appropriately diluted with water, for example, sterile water. Then, the chitosan solution may be filtered with a filter having a pore size of 0.5 to 2 μm, for example 1 μm (for example, cellulose filter) and the filtrate may be used in the following step.

The RNAi molecule which suppresses expression of CHST15 gene can be usually provided in the state of a solution containing the RNAi molecule in a proper buffer and produced by contracted manufacture of a manufacturer.

The RNAi molecule is mixed with chitosan to form a complex (RNAi molecule-chitosan complex) by, for example, electrostatic interaction. In the RNAi molecule-chitosan complex, the ratio (molar ratio) of the RNAi molecules and glucosamine units constituting chitosan may be 1:200 to 1:5, 1:100 to 1:5, or 1:50 to 1:10. The RNAi molecule and chitosan may be mixed by blending, for example, a solution containing the RNAi molecule with a chitosan solution, and stirring them.

The obtained RNAi molecule-chitosan complex is dried by any drying method known in the art, such as lyophilization, vacuum drying, preferably lyophilization. Lyophilization may be carried out after a solution containing the complex is flow-casted onto a substrate such as a Teflon dish. Lyophilization can be appropriately performed by a commercially available lyophilizer.

Subsequently, chitosan in the RNAi molecule-chitosan complex dried is acetylated with an acetylating agent. Examples of the acetylating agent include anhydrous acetic acid and acetyl chloride. Anhydrous acetic acid is preferable. The acetylating agent may be used in the state of a solution prepared by dissolving it in an organic solvent such as methanol. The acetylating agent may have a concentration of, for example, 0.5 to 10% (v/v) and preferably 1 to 5% (v/v). Acetylation may be performed by adding such an acetylating agent to the RNAi molecule-chitosan complex dried. The reaction time for acetylation may be 1 to 5 hours and preferably 2 to 4 hours. Acetylation may be performed in nitrogen gas. The temperature for the acetylation process may be room temperature, for example 15 to 30° C. Owing to such an acetylation process, a complex comprising an RNAi molecule and an N-acetylated chitosan can be obtained. The degree of acetylation of N-acetylated chitosan may be usually 70 to 100% for example 80% or more, 90% or more, 95% or more, 98% or more or 99% or more.

The obtained complex comprising an RNAi molecule and an N-acetylated chitosan may be dried by any drying method such as lyophilization and vacuum drying, preferably lyophilization. The complex dried may be further subjected to a processing such as grinding, and granulation.

<Pharmaceutical Composition>

The present invention also provides a pharmaceutical composition comprising a complex, which comprises an RNAi molecule which suppresses expression of CHST15 gene and an N-acetylated chitosan, for treating or preventing a disease. In the present specification, "treating" refers to healing, mitigating or ameliorating a disease or symptom, and "preventing" refers to inhibiting, suppressing or delaying onset of a disease or symptom.

A target disease is not particularly limited as long as the complex of the present invention exerts its effect on the disease, but may be, for example, an inflammatory disease or a mucosal damage. The inflammatory disease refers to a disease accompanied with inflammation. The mucosal damage refers to a pathological change of the mucosal membrane and may include ulcer, erosion and edema. The site of a disease may be any positions of the body, and may be preferably the digestive tract. The digestive tract may include, for example, esophagus, stomach, and intestine (small intestine and large intestine). Examples of the small intestine include the duodenum, jejunum and ileum. Examples of the large intestine include the cecum, colon and rectum.

The disease may be a disease induced by a drug (for example, non-steroidal anti-inflammatory drug). The non-steroidal anti-inflammatory drug (NSAID) is widely used as an antipyretic, analgesic and anti-inflammatory agents, but at the same time it is known that the drug may have a side effect such as a mucosal damage of the digestive tract.

Specifically, examples of the disease include inflammatory bowel diseases (for example, ulcerative colitis, Crohn's disease), esophagitis, gastroenteritis, NSAID-induced enteritis (for example, NSAID-induced small intestine inflammation), intestinal Behcet's disease, simple ulcer, artificial ulcer after endoscopic resection of alimentary canal cancer, enteritis associated with a connective tissue disease, enteritis by radiation, ischemic enteritis, reflux esophagitis, Barrett's esophagus, drug-induced esophagitis or gastroenteritis, and drug resistant or refractory peptic ulcer (including ulcer resistant to Helicobacter pylori eradication therapy). Preferably, the disease may be inflammatory bowel disease, ulcerative colitis, Crohn's disease, gastroenteritis or NSAID-induced enteritis. Ulcerative colitis is an inflammatory disease producing ulcer and erosion mainly in the mucosal membrane of the large intestine. Crohn's disease is an inflammatory disease producing non-continuous ulcer and inflammation throughout the alimentary canal tract from the oral cavity to the anus.

The NSAID is not particularly limited as long as it can induce a mucosal damage in the digestive tract. Examples of NSAID include, for example, salicylic acid based NSAIDs (for example, aspirin and sodium salicylate), fenamic acid based NSAIDs (for example, mefenamic acid), arylacetate based NSAIDs (for example, indomethacin, etodolac, diclofenac sodium, sulindac, proglumetacin maleate and acemetacin), propionic acid based NSAIDs (for example, ibuprofen, naproxen, ketoprofen, loxoprofen and zaltoprofen), oxycam based NSAIDs (for example, piroxicam, meloxicam and lornoxicam) and basic anti-inflammatory drugs (tiaramide hydrochloride, emorfazone). In the present specification, arylacetate based NSAID is preferable and indomethacin is more preferable.

The pharmaceutical composition may comprise any pharmaceutical aids commonly used in the pharmaceutical field. Examples of the pharmaceutical aids that can be used include pharmaceutically acceptable various drug carriers or additives such as a carrier (solid or liquid carrier), an excipient, a stabilizer, an emulsifier, a surfactant, a binding agent, a disintegrant, a lubricant, a flavoring agent, a solubilizing agent, a suspending agent, a coating agent, a colorant, a corrigent, a preservative and a buffer. Specifically, examples of the pharmaceutical aids include water, physiological saline, other aqueous solvents, pharmaceutically acceptable organic solvents, mannitol, microcrystalline cellulose, starch, glucose, calcium, polyvinyl alcohol, collagen, polyvinylpyrrolidone, carboxyvinyl polymer, sodium alginate, water-soluble dextran, water soluble dextrin, sodium carboxymethyl starch, gum Arabic, pectin, xanthan gum, casein, gelatin, agar, propylene glycol, glycerin, polyethylene glycol, vaseline, paraffin, stearyl alcohol, stearic acid, sorbitol and lactose. The pharmaceutical aids are selected appropriately or in combination depending on the dosage form of the formulation.

According to the present invention, a pharmaceutical composition can be orally or parenterally administered (for example, transrectal administration, transmucosal administration, intravenous administration, intraarterial administration, or transdermal administration) and particularly preferably administered orally and transrectally.

Examples of the dosage form suitable for oral administration may include a solid formulation (tablet, pill, sublingual formulation, capsule, trochisci, drop), a granule, a powder, a dust and a liquid. The solid formulation may be a formulation coated with a coating agent known in the art, for example, a sugar-coated tablet, a gelatin tablet, an enteric coated tablet, a film coated tablet, a double tablet or a multi-layer tablet. The coating agent may be provided in order to release an active ingredient or enhance absorbability of an active ingredient at a target site of the body.

In parenteral administration, dosage forms suitable for individual administration methods can be appropriately used. Examples of the dosage form suitable for parenteral administration may include a suppository, an injection, drip infusion, endermic liniment, an eye drop, a nasal drop, an inhalant, a suspending agent, an emulsion, a cream, a paste agent, a gel agent, an ointment and a plaster.

The pharmaceutical composition of the present invention can be administered to a living body in a pharmaceutically effective amount for treating or preventing a target disease. In the present specification, "pharmaceutically effective amount" refers to a dose of the RNAi molecule comprised in the pharmaceutical composition of the present invention, which is required for treating or preventing a target disease, with no or almost no harmful side effect on the living body to be administered. Specific dose is determined depending on each subject, based on the degree of progression or severity of a disease, systemic health condition, age, sex, body weight and resistance to a treatment for example, by a doctor. For example, in the case of orally administering the pharmaceutical composition of the present invention, the pharmaceutical composition may be usually administered in an amount, by weight of the RNAi molecule which suppresses expression of CHST15 gene, of 0.001 to 1000 mg/body weight kg/day, for example, 0.01 to 100 mg/body weight kg/day or 0.1 to 10 mg/body weight kg/day. The pharmaceutical composition of the present invention can be administered in a single dose based on, for example, a therapeutic program instructed by a doctor or may be administered to a subject by dividing the dose into several portions or several tens of portions, at predetermined intervals, for example, 1 day, 2 days, 3 days, 4 days, 5 days, 6 days, 1 week, 2 weeks, 3 weeks, 1 month, 2 months, 6 months or one year.

The pharmaceutical composition of the present invention may be administered in combination with other drugs (for example, a drug for the target disease to be treated or prevented by the pharmaceutical composition of the present invention or NSAID). In the case of combined administration, these drugs may be used as a combination preparation for simultaneous administration, or as a separate formulation to be independently administered in combination. The combined administration includes simultaneous administration and continuous administration.

The subject to which the pharmaceutical composition of the present invention is to be administered may be an animal, for example, a mammal (for example, human, monkey, bovine, mouse, rat, dog). If the target disease to be treated or prevented is a disease induced by a drug (for example, NSAID), the subject may be a patient to which the drug is administered.

The present invention also provides a method for treating or preventing a disease, comprising administering the pharmaceutical composition according to the present invention to a subject in need thereof. The present invention also relates to an inflammatory disease therapy or prophylactic agent or mucosal healing accelerator comprising a complex comprising an RNAi molecule which suppresses expression of CHST15 gene and an N-acetylated chitosan. The present invention also provides a method for producing a pharmaceutical composition according to the present invention, comprising a step of mixing a complex comprising an RNAi molecule which suppresses expression of CHST15 gene and an N-acetylated chitosan with a pharmaceutically acceptable carrier.

The pharmaceutical composition comprising a complex comprising an RNAi molecule which suppresses expression of CHST15 gene and an N-acetylated chitosan is particularly useful for treating or preventing an inflammatory disease or mucosal damage of the digestive tract.

EXAMPLES

The present invention is more specifically described by presenting Examples below; however, the technical scope of the present invention is not limited by these Examples.

Example 1

Effect of CHST15 siRNA/N-acetylated chitosan complex administered to DSS-induced acute colitis model mouse A CHST15 siRNA/N-acetylated chitosan complex was orally administered to model mice suffering dextran sulfate sodium (DSS)-induced colitis, and then, the RNAi effect and therapeutic effect of the complex were examined. The DSS-induced colitis (mouse) model is generally used as a standard experimental model of an inflammatory bowel disease such as mouse ulcerative colitis and Crohn's disease.

<Materials and Methods>

(siRNA/N-acetylated Chitosan Complex)

A method for preparing a CHST15 siRNA/N-acetylated chitosan complex and a negative control, i.e., siRNA (N.C.)/N-acetylated chitosan complex, will be described below. More specifically, these complexes were prepared in the same manner as described in Kai E et al., Pharmaceutical Research 21: 838-843 (2004) except that siRNA was used in place of plasmid DNA.

Chitosan, which is manufactured by Carbosynth Limited (UK), had a degree of deacetylation of at least 90% (in other words, degree of acetylation: 10% or less). Chitosan (2 g) was dissolved in 50 mL of 5% (v/v) acetic acid, and a 2 M sodium hydroxide was added so as to obtain pH of 4.2, and then, the volume of the chitosan solution was prepared to be 100 mL with sterile water. In consequence, a chitosan solution (2% w/v) was obtained. The chitosan solution was filtered under reduced pressure by a cellulose filter (pore size: 1 μm) and the filtrate was kept at room temperature until use.

The antisense strand and sense strand of siRNA, which suppresses expression of CHST15 gene (CHST15 siRNA) used in this Example, consist of the nucleotide sequences shown in SEQ ID NO: 3 and 4, respectively. Two RNA strands of the negative control siRNA consist of the nucleotide sequences shown in SEQ ID NO: 7 and 8, respectively. CHST15 siRNA and siRNA of negative control were synthesized by a contracted manufacturer, BioSpring GmbH (Germany).

The chitosan solution (2% w/v) prepared above was gently mixed with the CHST15 siRNA solution or siRNA solution of the negative control to obtain a solution containing a CHST15 siRNA/chitosan complex or a solution containing a siRNA of negative control /chitosan complex (100 mg siRNA/mL). The ratio (molar ratio) of CHST15 siRNA and glucosamine units constituting chitosan in the solution was about 1:21. Subsequently, the solution was flow-casted on a Teflon dish (diameter: 60 mm) and lyophilized overnight. The lyophilized-complex was subjected to an N-acetylation treatment performed in 3% (v/v) anhydrous acetic acid in methanol at room temperature in nitrogen gas for 3 hours. The obtained product was lyophilized overnight. In this manner, a CHST15 siRNA/N-acetylated chitosan complex and siRNA (N.C.)/N-acetylated chitosan complex which is a negative control were obtained.

(Animals)

Eight week-old female C57BL/6J mice were obtained from Japan SLC (Shizuoka, Japan). All animals used in this Example were raised in accordance with the guidelines for animal experimentation defined by the Japanese Pharmaceutical Society. The animals were kept in an animal facility under the conventional conditions, more specifically, a clean cage of a controlled room temperature (22 to 28° C.) and humidity (35 to 55%). The animal (mouse) was housed in polycarbonate cages (KN-600, Natsume Seisakusho, Co., Ltd., Japan) at most 3 mice per cage. The mice were permitted to freely take a sterilized regular diet and distilled water.

(Induction of Colitis)

Dextran sulfate sodium (DSS) was purchased from MP Biomedicals, LLC. The mice were allowed to freely take a 2.5% (w/v) DSS aqueous solution for 3 days (the first day the DSS aqueous solution was given was defined as Day 0; the solution was fed on Day 0, 1 and 2) to induce an acute colitis.

(Administration of siRNA/N-acetylated Chitosan Complex)

The following three groups were treated as follows:

Group 1: Normal mice (neither DSS nor complex were administered)

Group 2: Mice with DSS-induced colitis, a siRNA (N.C.)/N-acetylated chitosan complex as a negative control, was administered Group 3: Mice with DSS-induced colitis, a CHST15 siRNA/N-acetylated chitosan complex was administered Each of the groups was constituted of 5 mice. To mice with induced colitis of Group 2 and Group 3, a N.C./N-acetylated chitosan complex and a CHST15 siRNA/N-acetylated chitosan complex were orally administered, respectively on Day 0, 1 and 2. For administration, physiological saline (Otsuka Pharmaceutical Factory, Inc., Japan) was used as a vehicle. Administration was performed once a day, at a dose of 10 μg siRNA per mouse (a volume of 10 mL/kg). On Day 3, the mice were slaughtered, and effectiveness of the complex was evaluated.

(Measurement of Disease Activity Index)

Disease activity index (DAI) of the mice on Day 3 was calculated by adding rating evaluation indexes on weight loss, fecal occult blood and stool consistency. Evaluation criteria of weight loss, fecal occult blood and stool consistency are shown in Table 1.

TABLE 1

Evaluation criteria of weight loss, fecal occult blood and stool consistency

| Index | Weight loss | Fecal occult blood | Stool consistency |
|---|---|---|---|
| 0 | None | None | Normal |
| 1 | 1~5% | Hemoccult test (+) | — |
| 2 | 6~10% | Hemoccult test (++) | Loose stool |
| 3 | 11~15% | Hemoccult test (+++) | — |
| 4 | >15% | Significant bleeding | Diarrhea |

(Histopathology)

Distal colon (large intestine) (about 1.5 to 2.0 cm) was fixed in 10% neutral buffered formalin (Wako Pure Chemical Industries Ltd., Japan), embedded in paraffin and sliced into sections of 4 μm, followed by staining with HE. The sections were observed under a microscope. Histological score was calculated by adding rating evaluation indexes on intestinal epithelial damage and inflammatory infiltration. The evaluation criteria of the intestinal epithelial damage and inflammatory infiltration are shown in Table 2.

TABLE 2

Evaluation criteria of the intestinal epithelial damage and inflammatory infiltration

| Index | Intestinal epithelial damage | Inflammatory infiltration |
|---|---|---|
| 0 | Normal | No infiltration |
| 1 | Loss of goblet cells | Infiltration around crypt base |
| 2 | Loss of goblet cells in larger area | Infiltration reaching conjunctival muscle plate |
| 3 | Loss of crypts | Extensive infiltration reaching conjunctival muscle plate and |

TABLE 2-continued

Evaluation criteria of the intestinal epithelial damage and inflammatory infiltration

| Index | Intestinal epithelial damage | Inflammatory infiltration |
|---|---|---|
| 4 | Loss of crypts in larger area | mucosal thickening with many edemas Infiltration under mucosal membrane |

(Quantitative RT-PCR)

Total RNA was extracted from colon samples with RNAiso (Takara Bio Inc., Japan) in accordance with manufacturer's instructions. RNA (1 µg) was reverse-transferred using a reaction mixture (a final volume of 20 µL) containing 4.4 mM $MgCl_2$ (F. Hoffmann-La Roche, Switzerland), 40 U RNase inhibitor (Toyobo Co., Ltd., Japan), 0.5 mM dNTP (Promega, USA), 6.28 µM random hexamer (Promega), 5× first strand buffer (Promega), 10 mM dithiothreitol (Invitrogen) and 200 U MMLV-RT (Invitrogen). The reaction was performed at 37° C. for one hour and thereafter at 99° C. for 5 minutes. Real time PCR was performed using real time PCR DICE and SYBR premix Taq (Takara Bio Inc.). The sequences of the primers for CHST15 gene are shown in SEQ ID NOs: 9 and 10. The sequences of the primers for TNF-α gene are shown in SEQ ID NOs: 11 and 12. The sequences of the primers for MCP-1 gene are shown in SEQ ID NOs: 13 and 14. The sequences of the primers for ROR-γ gene are shown in SEQ ID NOs: 15 and 16. The sequences of the primers for 36B4 gene are shown in SEQ ID NOs: 17 and 18. To calculate the relative mRNA expression levels, the expression levels of individual genes (CHST15, TNF-α, MCP-1 and ROR-γ) were normalized based on the expression level of reference gene 36B4.

(Statistical Test)

Statistical tests were performed on DAI, colon length, histological score and relative gene expression level using the Bonferroni Multiple Comparison Test by GraphPad Prism 4 (GraphPad Software, USA). P values<0.05 were considered statistically significant. A trend or tendency was assumed when a one-tailed t test returned P values<0.05. The results were expressed by means±standard deviation. In the drawing, P value<0.05 was indicated by "*", P value<0.01 by "", P value<0.001 by "*", P value≥0.05 by "n.s." (no significant difference).

<Results>

(Disease Activity Index)

The results of disease activity index (DAI) are shown in FIG. 1. DAI measured in the N.C. administration group (Group 2) of the colitis model mice was significantly increased compared to that of the normal group (Group 1). DAI measured in the CHST15 siRNA administration group (Group 3) of the colitis model mice showed a significantly reduction compared to that of the N.C. administration group (Group 2). From the results, it was demonstrated that the CHST15 siRNA/N-acetylated chitosan complex suppresses colitis activity.

(Colon Length)

Figure 2:
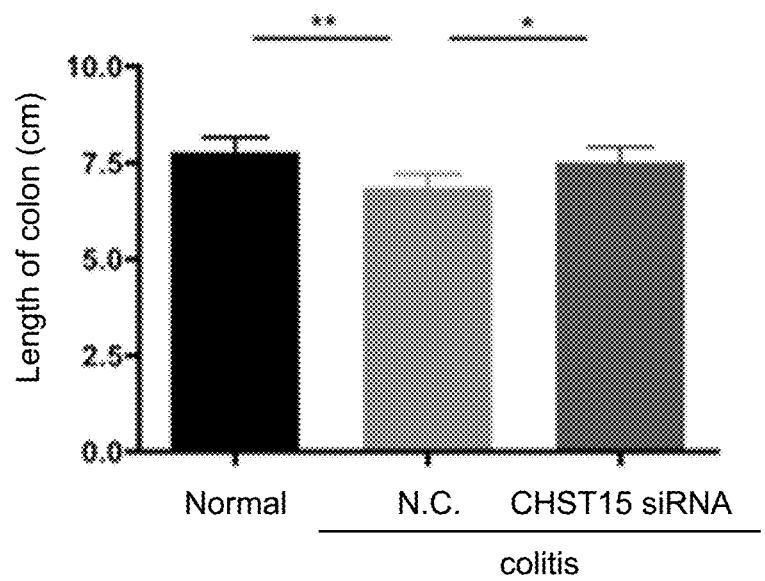
FIG. 2 is a graph showing the length of the colon of DSS-induced colitis model mice.

The results of colon length measurement are shown in FIG. 2. The colon length of the N.C. administration group of the colitis model mice (Group 2) on Day 3 was significantly short compared to that of the normal group (Group 1). In contrast, the colon length of the CHST15 siRNA administration group of the colitis model mice (Group 3) was significantly long compared to the N.C. administration group (Group 2). From the results, it was demonstrated that the CHST15 siRNA/N-acetylated chitosan complex prevents the colon from shortening by the colitis.

(Histological Analysis)

Figure 3:
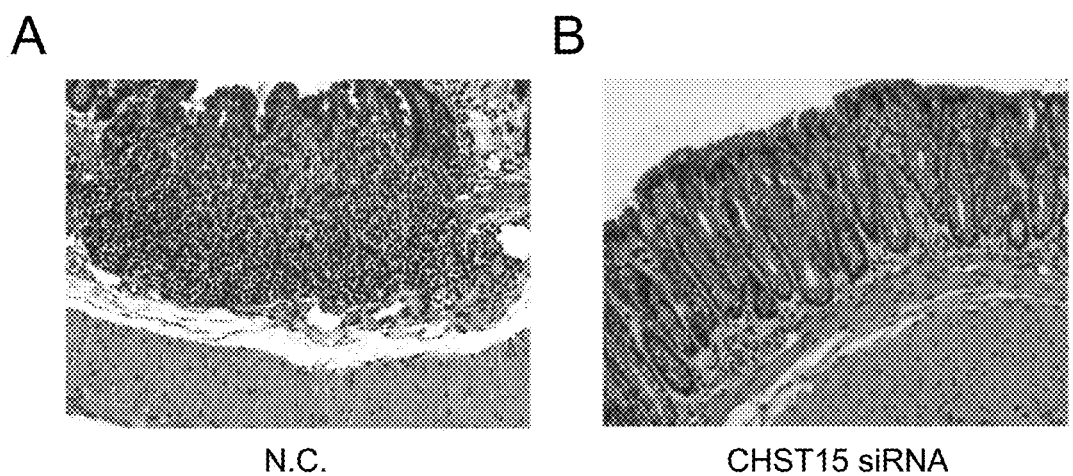
FIG. 3 shows photomicrographs of HE-stained sections of the colons of DSS-induced colitis model mice.
Figure 4:
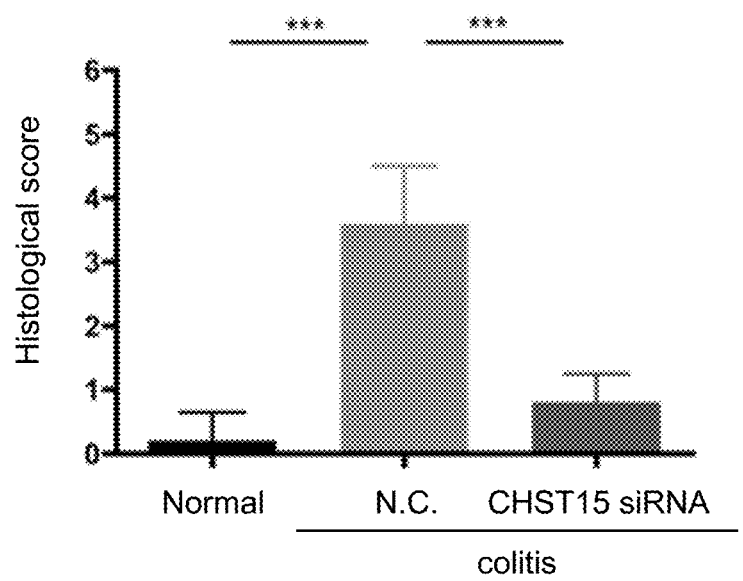
FIG. 4 is a graph showing histological scores of the colons of DSS-induced colitis model mice.

Intestinal epithelial damage and inflammatory infiltration were evaluated by using colonic sections stained with HE. Photomicrographs of typical HE-stained sections are shown in FIG. 3. Massive ulceration was not observed in any groups on Day 3; however focal ulcerative lesion with inflammatory infiltration was observed in the N.C. administration group of the colitis model mice (Group 2) (FIG. 3A). All of these lesions were apparent in the lamina propria associated with the loss of goblet cells in Group 2. In the CHST15 siRNA administration group of the colitis model mice (Group 3), slight crypt damage and inflammatory infiltration were reduced (FIG. 3B). The histological score of the CHST15 siRNA administration group of the colitis model mice (Group 3) was significantly reduced compared to the N.C. administration group (Group 2) (FIG. 4). From these results, it was demonstrated that the CHST15 siRNA/N-acetylated chitosan complex also has histological therapeutic effect on the colitis and does not induce inflammation.

(Gene Expression Analysis)

Figure 5:
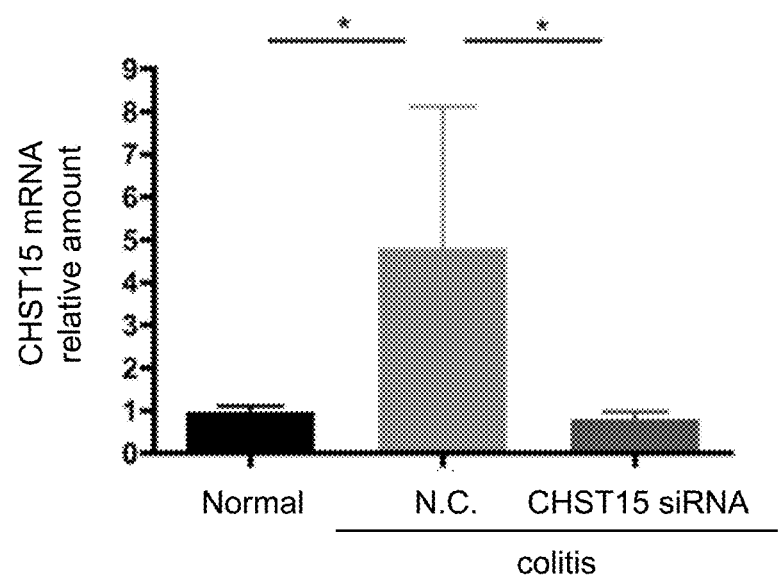
FIG. 5 is a graph showing CHST15 gene expression in the colons of DSS-induced colitis model mice.

CHST15 gene expression results are shown in FIG. 5. CHST15 mRNA level in the colon of the N.C. administration group of the colitis model mice (Group 2) was significantly increased compared to the normal group (Group 1). In contrast, CHST15 mRNA level in the colon of the CHST15 siRNA administration group of the colitis model mice (Group 3) was significantly reduced compared to the N.C. administration group (Group 2). Furthermore, there were no significant differences in TNF-α, MCP-1 and ROR-γ mRNA (expression) levels between the CHST15 siRNA administration group (Group 3) and the N.C. administration group (Group 2) of the colitis model mice, although the expression levels are known to be increased by inflammation. From these results, it was demonstrated that CHST15 siRNA/N-acetylated chitosan complex specifically decreases in CHST15 mRNA level in the colon (large intestine) and does not induce inflammation.

Example 2

Effect of CHST15 siRNA/N-acetylated chitosan complex administered to NSAID-induced small intestine inflammation model mouse It is known that a non-steroidal anti-inflammatory drug (NSAID) induces mucosal damage and inflammation in the digestive tract, as a side effect. In this Example, RNAi effect and therapeutic effect of CHST15 siRNA/N-acetylated chitosan complex orally administered in model mice of small intestine inflammation induced by indomethacin as NSAID, were examined.

(N-acetylated Chitosan/siRNA Complex)

A CHST15 siRNA/N-acetylated chitosan complex and a siRNA (N.C.)/N-acetylated chitosan complex as a negative control were produced by the method described in Example 1.

(Animals)

Seven to eight week-old female C57BL/6J mice were obtained from Japan SLC (Shizuoka, Japan) and raised in the same rearing conditions as described in Example 1.

(Induction of Small Intestine Inflammation)

On Day 0, indomethacin (Wako Pure Chemical Industries Ltd.) as NSAID was subcutaneously administered to mice in a dose of 10 mg per body weight (1 kg) to induce small intestine inflammation.

(Administration of N-Acetylated Chitosan/siRNA Complex)

The following four groups were treated as follows:

Group 1: Normal (neither NSAID nor complex were administered);

Group 2: NSAID-induced small intestine inflammation; a mock were administered;

Group 3: NSAID-induced small intestine inflammation; siRNA (N.C.)/N-acetylated chitosan complex as a negative control were administered; and Group 4: NSAID-induced small intestine inflammation; CHST15 siRNA/N-acetylated chitosan complex were administered.

Each of the groups was constituted of 4 mice. To the mice of Group 2, physiological saline (Otsuka Pharmaceutical Factory, Inc. Japan) as a vehicle was administered. To the mice of Group 3 and Group 4, the N.C./N-acetylated chitosan complex and the CHST15 siRNA/N-acetylated chitosan complex were orally and forcibly administered, respectively. The administration was performed once on Day 0 after completion of NSAID administration (induction of small intestine inflammation) in a dose of 10 µg siRNA per mouse. On Day 1, the mice were slaughtered, and effectiveness of the complex was evaluated.

(Evaluation Method for Effectiveness of Complex)

CHST15 mRNA expression level was determined by quantitative RT-PCR in the same manner as described in Example 1 except that the jejunum was used in place of the colon. In the jejunum, the number of visible ulcers was counted, and ulceration score was determined. A statistical test was carried out in the same manner as described in Example 1.

<Results>

(Gene Expression Analysis)

Figure 6:
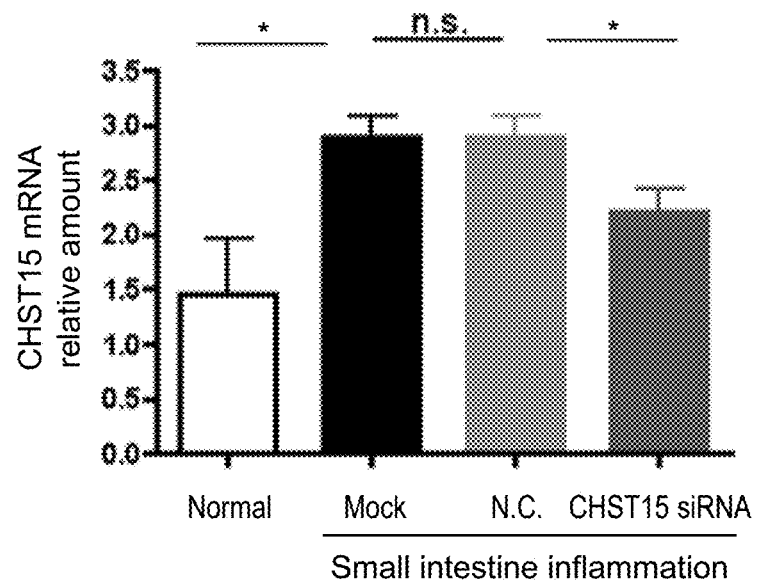
FIG. 6 is a graph showing CHST15 gene expression in the jejunum of NSAID (non-steroidal anti-inflammatory drug) induced small intestine inflammation model mice.

CHST15 gene expression results are shown in FIG. 6. CHST15 mRNA level in the jejunum (small intestine) of the mock administration group (Group 2) and N.C. administration group (Group 3) of the small intestine inflammation model mice were significantly increased compared to the normal group (Group 1). In contrast, CHST15 mRNA level in the jejunum of the CHST15 siRNA administration group of the small intestine inflammation model mice (Group 4) was significantly decreased compared to those of the mock administration group (Group 2) and the N.C. administration group (Group 3). From the results, it was demonstrated that the CHST15 siRNA/N-acetylated chitosan complex decreases CHST15 mRNA level in the jejunum (small intestine).

(Ulceration Score)

Figure 7:
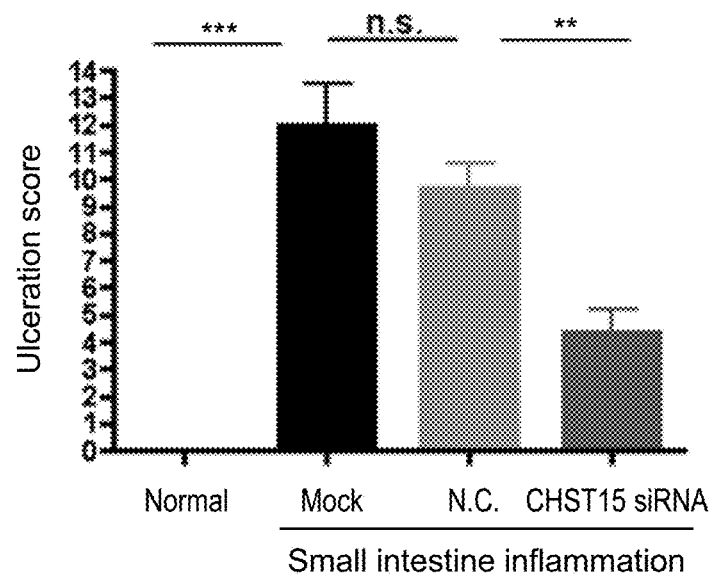
FIG. 7 is a graph showing ulcer scores of the jejunum in NSAID-induced small intestine inflammation model mice.

The results of ulceration score (number of ulcers) are shown in FIG. 7. The number of ulcers in the jejunum (small intestine) was significantly increased in the mock administration group (Group 2) and the N.C. administration group (Group 3) of the small intestine inflammation model mice, compared to the normal group (Group 1). In contrast, the number of ulcers in the jejunum was significantly decreased in the CHST15 siRNA administration group (Group 4) of the small intestine inflammation model mice, compared to the mock administration group (Group 2) and the N.C. administration group (Group 3). From the results, it was demonstrated that CHST15 siRNA/N-acetylated chitosan complex decreases the number of NSAID-induced ulcers in the jejunum (small intestine) and has a suppressive effect on NSAID-induced small intestine inflammation.

All publications, patents and patent applications are incorporated in their entirety in the present specification by reference.

The invention claimed is:

1. A complex comprising an N-acetylated chitosan and an RNAi molecule which suppresses expression of CHST15 gene, wherein the N-acetylated chitosan has a degree of acetylation of 70 to 100%.

2. The complex according to claim 1, wherein the RNAi molecule is siRNA or shRNA.

3. The complex according to claim 1, wherein the RNAi molecule comprises an antisense strand comprising a nucleotide sequence shown in SEQ ID NO: 1 and a sense strand comprising a nucleotide sequence complementary to the antisense strand.

4. A pharmaceutical composition comprising the complex according to claim 1, for treating or preventing a disease.

5. The pharmaceutical composition according to claim 4, for use in oral administration or transrectal administration.

6. The pharmaceutical composition according to claim 4, wherein the disease is an inflammatory disease or mucosal damage of a digestive tract.

7. The pharmaceutical composition according to claim 6, wherein the inflammatory disease or mucosal damage is selected from the group consisting of inflammatory bowel disease, ulcerative colitis, Crohn's disease, esophagitis, gastroenteritis, NSAID-induced enteritis, intestinal Behcet's disease, simple ulcer, artificial ulcer after endoscopic resection of alimentary canal cancer, enteritis associated with a connective tissue disease, enteritis by radiation, ischemic enteritis, reflux esophagitis, Barrett's esophagus, drug-induced esophagitis or gastroenteritis, and drug resistant or refractory peptic ulcer.

* * * * *

SEQUENCE LISTING

```
<160> NUMBER OF SEQ ID NOS: 18

<210> SEQ ID NO 1
<211> LENGTH: 25
<212> TYPE: RNA
<213> ORGANISM: Artificial Sequence
<220> FEATURE:
<223> OTHER INFORMATION: An artificially synthesized siRNA sequence

<400> SEQUENCE: 1
gauuguauuc aucuugcucu gcucc                                          25

<210> SEQ ID NO 2
<211> LENGTH: 25
<212> TYPE: RNA
<213> ORGANISM: Artificial Sequence
<220> FEATURE:
<223> OTHER INFORMATION: An artificially synthesized siRNA sequence

<400> SEQUENCE: 2
ggagcagagc aagaugaaua caauc                                          25

<210> SEQ ID NO 3
<211> LENGTH: 27
<212> TYPE: RNA
<213> ORGANISM: Artificial Sequence
<220> FEATURE:
<223> OTHER INFORMATION: An artificially synthesized siRNA sequence

<400> SEQUENCE: 3
```

-continued

```
gauuguauuc aucuugcucu gcuccau                                      27
```

<210> SEQ ID NO 4
<211> LENGTH: 27
<212> TYPE: RNA
<213> ORGANISM: Artificial Sequence
<220> FEATURE:
<223> OTHER INFORMATION: An artificially synthesized siRNA sequence

<400> SEQUENCE: 4

```
ggagcagagc aagaugaaua caaucag                                      27
```

<210> SEQ ID NO 5
<211> LENGTH: 4713
<212> TYPE: DNA
<213> ORGANISM: Homo sapiens
<220> FEATURE:
<221> NAME/KEY: CDS
<222> LOCATION: (514)..(2199)

<400> SEQUENCE: 5

```
ggaaatctgg cattttttaa agtttgcgcc ccacaaagag gaaatattcc aaaggtactc   60
aggatgtaaa aggggagatc ttcacagatg cctccgtgga tggcatggca atccatccat  120
caatgagaag accatgattt cttttaattt tctgtgtgtt tccacattcc ccagtgagaa  180
ttcttccacc ttttttgtg ccatgggaaa aacctgaagg gcaggcagag ctgctcccga  240
acttgtgacc ttctctgagg ttgcagcggc tcttgtagaa catgactctg gacatcact   300 tccttttgtt ttctttcgga gctgaaccaa agaatgtgca ccctctttct ctagtgctgt  360
ggtgtctgct tattttttgta tttgtgcttt ccatccatct tctgtgatca caaggcattc  420
ttaaggtttt ctagcacgac ttgcggacat ccagactcgt gggggggccca cccatggctc  480 ggtaagccag cagcccaggg cactggcact acc atg agg cac tgc att aat tgc   534
                                    Met Arg His Cys Ile Asn Cys
                                      1               5 tgc ata cag ctg tta ccc gac ggc gca cac aag cag cag gtc aac tgc   582
Cys Ile Gln Leu Leu Pro Asp Gly Ala His Lys Gln Gln Val Asn Cys
         10                  15                  20 caa ggg ggc ccc cat cac ggt cac cag gcg tgc ccc acg tgc aaa gga   630
Gln Gly Gly Pro His His Gly His Gln Ala Cys Pro Thr Cys Lys Gly
 25                  30                  35 gaa aac aaa att ctg ttt cgt gtg gac agt aag cag atg aac ttg ctt   678
Glu Asn Lys Ile Leu Phe Arg Val Asp Ser Lys Gln Met Asn Leu Leu
 40                  45                  50                  55 gct gtt ctc gaa gtg agg act gaa ggg aac gaa aac tgg ggt ggg ttt   726
Ala Val Leu Glu Val Arg Thr Glu Gly Asn Glu Asn Trp Gly Gly Phe
                 60                  65                  70 ttg cgc ttc aaa aag ggg aag cga tgt agc ctc gtt ttt gga ctg ata   774
Leu Arg Phe Lys Lys Gly Lys Arg Cys Ser Leu Val Phe Gly Leu Ile
             75                  80                  85 ata atg acc ttg gta atg gct tct tac atc ctt tct ggg gcc cac caa   822
Ile Met Thr Leu Val Met Ala Ser Tyr Ile Leu Ser Gly Ala His Gln
         90                  95                 100 gag ctt ctg atc tca tca cct ttc cat tac gga ggc ttc ccc agc aac   870
Glu Leu Leu Ile Ser Ser Pro Phe His Tyr Gly Gly Phe Pro Ser Asn
105                 110                 115 ccc agc ttg atg gac agc gaa aac cca agt gac aca aag gag cat cac   918
Pro Ser Leu Met Asp Ser Glu Asn Pro Ser Asp Thr Lys Glu His His
120                 125                 130                 135 cac caa tcc tct gta aat aat att tca tac atg aag gac tat cca agc   966
His Gln Ser Ser Val Asn Asn Ile Ser Tyr Met Lys Asp Tyr Pro Ser
```

```
                        140                 145                 150
att aaa tta att atc aac agc atc aca act agg att gag ttc acg acc         1014
Ile Lys Leu Ile Ile Asn Ser Ile Thr Thr Arg Ile Glu Phe Thr Thr
                155                 160                 165 aga cag ctc cca gac tta gaa gac ctt aag aag cag gag ttg cat atg         1062
Arg Gln Leu Pro Asp Leu Glu Asp Leu Lys Lys Gln Glu Leu His Met
            170                 175                 180 ttt tca gtc atc ccc aac aaa ttc ctt cca aac agt aag agc ccc tgt         1110
Phe Ser Val Ile Pro Asn Lys Phe Leu Pro Asn Ser Lys Ser Pro Cys
        185                 190                 195 tgg tac gag gag ttc tcg ggg cag aac acc acc gac ccc tac ctc acc         1158
Trp Tyr Glu Glu Phe Ser Gly Gln Asn Thr Thr Asp Pro Tyr Leu Thr
200                 205                 210                 215 aac tcc tac gtg ctc tac tcc aag cgc ttc cgc tcc acc ttc gac gcc         1206
Asn Ser Tyr Val Leu Tyr Ser Lys Arg Phe Arg Ser Thr Phe Asp Ala
                220                 225                 230 ctg cgc aag gcc ttc tgg ggc cac ctg gcg cac gcg cac ggg aag cac         1254
Leu Arg Lys Ala Phe Trp Gly His Leu Ala His Ala His Gly Lys His
            235                 240                 245 ttc cgc ctg cgc tgc ctg ccg cac ttc tac atc ata ggg cag ccc aag         1302
Phe Arg Leu Arg Cys Leu Pro His Phe Tyr Ile Ile Gly Gln Pro Lys
        250                 255                 260 tgc ggg acc aca gac ctc tat gac cgc ctg cgg ctg cac cct gag gtc         1350
Cys Gly Thr Thr Asp Leu Tyr Asp Arg Leu Arg Leu His Pro Glu Val
265                 270                 275 aag ttc tcc gcc atc aag gag cca cac tgg tgg acc cgg aag cgc ttt         1398
Lys Phe Ser Ala Ile Lys Glu Pro His Trp Trp Thr Arg Lys Arg Phe
                280                 285                 290                 295 gga atc gtc cgc cta aga gat ggg ctg cga gac cgc tat ccc gtg gaa         1446
Gly Ile Val Arg Leu Arg Asp Gly Leu Arg Asp Arg Tyr Pro Val Glu
            300                 305                 310 gat tat ctg gac ctc ttt gac ctg gcc gca cac cag atc cat caa gga         1494
Asp Tyr Leu Asp Leu Phe Asp Leu Ala Ala His Gln Ile His Gln Gly
        315                 320                 325 ctg cag gcc agc tct gca aag gag cag agc aag atg aat aca atc att         1542
Leu Gln Ala Ser Ser Ala Lys Glu Gln Ser Lys Met Asn Thr Ile Ile
            330                 335                 340 atc ggg gag gcc agt gcc tcc acg atg tgg gat aat aat gcc tgg acg         1590
Ile Gly Glu Ala Ser Ala Ser Thr Met Trp Asp Asn Asn Ala Trp Thr
345                 350                 355 ttc ttc tac gac aac agc acg gat ggc gag cca ccg ttt ctg acg cag         1638
Phe Phe Tyr Asp Asn Ser Thr Asp Gly Glu Pro Pro Phe Leu Thr Gln
360                 365                 370                 375 gac ttc atc cac gcc ttt cag cca aat gcc aga ctg att gtc atg ctc         1686
Asp Phe Ile His Ala Phe Gln Pro Asn Ala Arg Leu Ile Val Met Leu
            380                 385                 390 agg gac cct gtg gag agg ttg tac tca gac tat ctc tac ttt gca agt         1734
Arg Asp Pro Val Glu Arg Leu Tyr Ser Asp Tyr Leu Tyr Phe Ala Ser
        395                 400                 405 tcg aat aaa tcc gcg gac gac ttc cat gag aaa gtg aca gaa gca ctg         1782
Ser Asn Lys Ser Ala Asp Asp Phe His Glu Lys Val Thr Glu Ala Leu
                410                 415                 420 cag ctg ttt gaa aat tgc atg ctt gat tat tca ctg cgc gcc tgc gtc         1830
Gln Leu Phe Glu Asn Cys Met Leu Asp Tyr Ser Leu Arg Ala Cys Val
            425                 430                 435 tac aac aac acc ctc aac aac gcc atg cct gtg agg ctc cag gtt ggg         1878
Tyr Asn Asn Thr Leu Asn Asn Ala Met Pro Val Arg Leu Gln Val Gly
440                 445                 450                 455 ctc tat gct gtg tac ctt ctg gac tgg ctc agc gtt ttt gac aag caa         1926
```

```
                Leu Tyr Ala Val Tyr Leu Leu Asp Trp Leu Ser Val Phe Asp Lys Gln
                                460                 465                 470 cag ttt ctc att ctt cgc ctg gaa gat cat gca tcc aac gtc aag tac        1974
Gln Phe Leu Ile Leu Arg Leu Glu Asp His Ala Ser Asn Val Lys Tyr
                475                 480                 485 acc atg cac aag gtc ttc cag ttt ctg aac cta ggg ccc tta agt gag        2022
Thr Met His Lys Val Phe Gln Phe Leu Asn Leu Gly Pro Leu Ser Glu
            490                 495                 500 aag cag gag gct ttg atg acc aag agc ccc gca tcc aat gca cgg cgt        2070
Lys Gln Glu Ala Leu Met Thr Lys Ser Pro Ala Ser Asn Ala Arg Arg
            505                 510                 515 ccc gag gac cgg aac ctg ggg ccc atg tgg ccc atc aca cag aag att        2118
Pro Glu Asp Arg Asn Leu Gly Pro Met Trp Pro Ile Thr Gln Lys Ile
520                 525                 530                 535 ctg cgg gat ttc tac agg ccc ttc aac gct agg ctg gcg cag gtc ctc        2166
Leu Arg Asp Phe Tyr Arg Pro Phe Asn Ala Arg Leu Ala Gln Val Leu
                540                 545                 550 gcg gat gag gcg ttt gcg tgg aag acg acg tga gagctgaatt gttgctgcac     2219
Ala Asp Glu Ala Phe Ala Trp Lys Thr Thr
                555                 560
```

| | |
|---|---|
| gtgctgggcc cgccaatgcc gtcatcatca ggattttaca aatctctttg cggggaactg | 2279 |
| tttcactcat ggtatggaaa accccaggac tctgccactc taggcacaca tgaattataa | 2339 |
| ccattttgga atttccttcg tgatgttcga gagctcagca atggacccct cacagagctc | 2399 |
| ctctatccga ggccattgga gacccagtt tctcaagaat tcagctctgc tctgagcgtc | 2459 |
| ctggagcttg gggatgcagc cagctggcct gcactgggtg tggagagaac cctagggaa | 2519 |
| ggcagcctgg ccctgcccgc ctccgccttc tggagagcct ctgggttctg agtcagcaag | 2579 |
| ccagaggtca tgccacaggc ctggctggaa cttacacttc acgttccctt ttttccccc | 2639 |
| tagagatggg gtctcgccgt gttgcacaga ctgtctgtat tcaatggcta tcttcacagg | 2699 |
| tgtgatcata ccacattcac ttctgaaaca ctcttgttgc gatcgctaac ctcactggga | 2759 |
| cagagaaccg cagtctttcg agaatggagg ctcttcattt ttttttctc ctttactcca | 2819 |
| aactcagccc tccagtttct tcagatgtaa accctgttaa cgtcactgtt tccaaaagga | 2879 |
| aaaaaataag tcagttttg gcagcacctt catctttctg acctcctcct attctgtcct | 2939 |
| tgtggactta tgtttaacat agaaaatgaa tgcgtttaaa acaaaaccac tttctgcatt | 2999 |
| taaccagtcc tggctctctc tctgctgcct cttcatacgt tttctcaaga acttcagttt | 3059 |
| ataattggaa gagaaatttt tgctgttaat gccagaatga gcaacctcaa ggaattgaac | 3119 |
| acttcttgga aaatctaggt aattcaagcc ctcatcaggt ttacaagatc atcagagaaa | 3179 |
| cagaggattt taattttag ttctggccgg ctacaggctc catttctctg ccttcccatt | 3239 |
| ggaaatagtt tatttccaca ttctccactg cgtgtggtca aagttcctca cccagcaagg | 3299 |
| gactatagat actcgtgtcc caattccaaa acacaatgca caagctgaac ttgggctgaa | 3359 |
| cgtggcgtgt tgagatttgg aatgaggttt ctaagagccg tgttcttcat ggaattttcc | 3419 |
| aggccacttg gcagcttggt ttaccgatgg atgggctaga gatcttgtcg tttcttggaa | 3479 |
| gtcacaggga agattgaaga gaacgcttga gcatccttgg caacagccca ggtgggacct | 3539 |
| ggatgaagct ttgcactcaa gtattgtcaa gggaagcttc ctgtgaacca aagttctcag | 3599 |
| gccaaggtct cgcccaccaa agccagaaag tgcaagcacc cgtctaccca gctctaactt | 3659 |
| gtatgtgtga gacagaccag gcttcggggg taggaggatc tgcagttgtt cagccgtctt | 3719 |
| tctgctggtg ttgtctttct gccatcagag aagggacaca cagcccgttc gaaggtgtgc | 3779 |

```
agagggctct gagcgccagg atggccaggg ctgttttgc tactgaagga gcgtgtgtcc      3839
tgaactccca cttgcaggga cagtccccac cttctctata gccggcactg ggagcagccg      3899
ccagcaggga aatctggcct gagcacaagg atgctttagg gagagatcac ttcagtgtgt      3959
gtgtatattt atttgcagta cagtgcgcgc gtgtgtgtgt gtgtacgcgc acgtgtgggt      4019
gagtgcgtct tctgagtggg ttctgttcag ttgctaatga ggctcctccg ctctggacac      4079
aaccctttta tagattaatt tctctgccaa ttaacttgtc attttcagta catattttac      4139
tattccacac caaccataat tacaacaagg gattttcttt atgcactcct atgcatgtga      4199
ataacatgtg gtgtaattct gcttcttaca gaagtattac tgaaggtatt atttccaata      4259
ttatttggtt tattatgcgg atctttttta tatatgcagt cccatcccctt ctgtgccact      4319
caatgccatc cagacatggt ttttccctcc aggggccttt ctctccagag ggcacttcgg      4379
ctgcctctgc ttcctctcat tcgaggcccg gctcttgctg acagaatagg ttccgttctg      4439
ggcggtggtt ctcgagcctg ccattcaaaa ccaaagcaaa ttggagcatt tctcacaaca      4499
tggtattgaa gttcctttt gttctcaaaa gttgtgaccg tgttaaattg tactcccta      4559
gtcctgtaag gtatgttaag tgaatcgcag ttacgctgta cttttattaa tatttaacat      4619
aattaaagat ggacccataa gagtgacgcc tgtggagcgc gtgctcttcc tctgcagcca      4679
aaaaaaaaaa aaaaaaaaa aaaaaaaaaa aaaa                                   4713
```

<210> SEQ ID NO 6
<211> LENGTH: 561
<212> TYPE: PRT
<213> ORGANISM: Homo sapiens

<400> SEQUENCE: 6

```
Met Arg His Cys Ile Asn Cys Cys Ile Gln Leu Leu Pro Asp Gly Ala
1               5                   10                  15

His Lys Gln Gln Val Asn Cys Gln Gly Gly Pro His His Gly His Gln
            20                  25                  30

Ala Cys Pro Thr Cys Lys Gly Glu Asn Lys Ile Leu Phe Arg Val Asp
        35                  40                  45

Ser Lys Gln Met Asn Leu Leu Ala Val Leu Glu Val Arg Thr Glu Gly
    50                  55                  60

Asn Glu Asn Trp Gly Gly Phe Leu Arg Phe Lys Lys Gly Lys Arg Cys
65                  70                  75                  80

Ser Leu Val Phe Gly Leu Ile Ile Met Thr Leu Val Met Ala Ser Tyr
                85                  90                  95

Ile Leu Ser Gly Ala His Gln Glu Leu Leu Ile Ser Ser Pro Phe His
            100                 105                 110

Tyr Gly Gly Phe Pro Ser Asn Pro Ser Leu Met Asp Ser Glu Asn Pro
        115                 120                 125

Ser Asp Thr Lys Glu His His His Gln Ser Ser Val Asn Asn Ile Ser
    130                 135                 140

Tyr Met Lys Asp Tyr Pro Ser Ile Lys Leu Ile Ile Asn Ser Ile Thr
145                 150                 155                 160

Thr Arg Ile Glu Phe Thr Thr Arg Gln Leu Pro Asp Leu Glu Asp Leu
                165                 170                 175

Lys Lys Gln Glu Leu His Met Phe Ser Val Ile Pro Asn Lys Phe Leu
            180                 185                 190

Pro Asn Ser Lys Ser Pro Cys Trp Tyr Glu Glu Phe Ser Gly Gln Asn
        195                 200                 205
```

```
Thr Thr Asp Pro Tyr Leu Thr Asn Ser Tyr Val Leu Tyr Ser Lys Arg
    210                 215                 220
Phe Arg Ser Thr Phe Asp Ala Leu Arg Lys Ala Phe Trp Gly His Leu
225                 230                 235                 240
Ala His Ala His Gly Lys His Phe Arg Leu Arg Cys Leu Pro His Phe
            245                 250                 255
Tyr Ile Ile Gly Gln Pro Lys Cys Gly Thr Thr Asp Leu Tyr Asp Arg
                260                 265                 270
Leu Arg Leu His Pro Glu Val Lys Phe Ser Ala Ile Lys Glu Pro His
            275                 280                 285
Trp Trp Thr Arg Lys Arg Phe Gly Ile Val Arg Leu Arg Asp Gly Leu
290                 295                 300
Arg Asp Arg Tyr Pro Val Glu Asp Tyr Leu Asp Leu Phe Asp Leu Ala
305                 310                 315                 320
Ala His Gln Ile His Gln Gly Leu Gln Ala Ser Ser Ala Lys Glu Gln
                325                 330                 335
Ser Lys Met Asn Thr Ile Ile Gly Glu Ala Ser Ala Ser Thr Met
                340                 345                 350
Trp Asp Asn Asn Ala Trp Thr Phe Phe Tyr Asp Asn Ser Thr Asp Gly
            355                 360                 365
Glu Pro Pro Phe Leu Thr Gln Asp Phe Ile His Ala Phe Gln Pro Asn
    370                 375                 380
Ala Arg Leu Ile Val Met Leu Arg Asp Pro Val Glu Arg Leu Tyr Ser
385                 390                 395                 400
Asp Tyr Leu Tyr Phe Ala Ser Ser Asn Lys Ser Ala Asp Phe His
                405                 410                 415
Glu Lys Val Thr Glu Ala Leu Gln Leu Phe Glu Asn Cys Met Leu Asp
                420                 425                 430
Tyr Ser Leu Arg Ala Cys Val Tyr Asn Asn Thr Leu Asn Asn Ala Met
            435                 440                 445
Pro Val Arg Leu Gln Val Gly Leu Tyr Ala Val Tyr Leu Leu Asp Trp
    450                 455                 460
Leu Ser Val Phe Asp Lys Gln Gln Phe Leu Ile Leu Arg Leu Glu Asp
465                 470                 475                 480
His Ala Ser Asn Val Lys Tyr Thr Met His Lys Val Phe Gln Phe Leu
                485                 490                 495
Asn Leu Gly Pro Leu Ser Glu Lys Gln Glu Ala Leu Met Thr Lys Ser
            500                 505                 510
Pro Ala Ser Asn Ala Arg Arg Pro Glu Asp Arg Asn Leu Gly Pro Met
            515                 520                 525
Trp Pro Ile Thr Gln Lys Ile Leu Arg Asp Phe Tyr Arg Pro Phe Asn
    530                 535                 540
Ala Arg Leu Ala Gln Val Leu Ala Asp Glu Ala Phe Ala Trp Lys Thr
545                 550                 555                 560
Thr
```

<210> SEQ ID NO 7
<211> LENGTH: 27
<212> TYPE: RNA
<213> ORGANISM: Artificial
<220> FEATURE:
<223> OTHER INFORMATION: An artificially synthesized siRNA sequence

<400> SEQUENCE: 7
acucgauucu auuaacaagg guaucac             27

<210> SEQ ID NO 8
<211> LENGTH: 27
<212> TYPE: RNA
<213> ORGANISM: Artificial
<220> FEATURE:
<223> OTHER INFORMATION: An artificially synthesized siRNA sequence

<400> SEQUENCE: 8
gauacccuug uuaauagaau cgaguua                                    27

<210> SEQ ID NO 9
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 9
gtgagttctg ctgcggtcca                                            20

<210> SEQ ID NO 10
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 10
agtccatgct gatgcccaga g                                          21

<210> SEQ ID NO 11
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 11
caggagggag aacagaaact cca                                        23

<210> SEQ ID NO 12
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 12
cctggttggc tgcttgctt                                             19

<210> SEQ ID NO 13
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 13
gcatccacgt gttggctca                                             19

<210> SEQ ID NO 14
<211> LENGTH: 23
<212> TYPE: DNA
<213> ORGANISM: Artificial
<220> FEATURE:

-continued

```
<223> OTHER INFORMATION: An artificially synthesized primer sequence

<400> SEQUENCE: 14
ctccagccta ctcattggga tca                                           23

<210> SEQ ID NO 15
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 15
tctgcaagac tcatcgacaa gg                                            22

<210> SEQ ID NO 16
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 16
cacatgttgg ctgcacagg                                                19

<210> SEQ ID NO 17
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 17
ttccaggctt tgggcatca                                                19

<210> SEQ ID NO 18
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 18
atgttcagca tgttcagcag tgtg                                          24
```